United States Patent [19]
Webb et al.

[11] Patent Number: 5,044,365
[45] Date of Patent: Sep. 3, 1991

[54] RATE-RESPONSIVE PACEMAKER

[76] Inventors: Stuart C. Webb, 5 Lingholm Way, Barnet, Hertfordshire; Leland M. Lewis, 43 Prince George Avenue, Oakwood London N14 4TL; Jayne A. Morris-Thurgood, 20 Pym Walk, Thame Oxfordshire, all of United Kingdom

[21] Appl. No.: 515,085

[22] Filed: Apr. 26, 1990

Related U.S. Application Data

[63] Continuation of Ser. No. 311,638, Jul. 16, 1989.

[30] Foreign Application Priority Data

Feb. 17, 1988 [GB] United Kingdom ................. 8803613
Aug. 12, 1988 [GB] United Kingdom ................. 8819268

[51] Int. Cl.$^5$ ............................................. A61N 1/00
[52] U.S. Cl. ............................... 128/419 PG; 128/782
[58] Field of Search .................. 128/419 PG, 419 PS, 128/784, 786, 782

[56] References Cited

U.S. PATENT DOCUMENTS

| | | | |
|---|---|---|---|
| 4,273,132 | 6/1981 | Hartlaub et al. | 128/419 PG |
| 4,340,062 | 7/1982 | Thompson et al. | 128/419 PG |
| 4,365,633 | 12/1982 | Loughmann et al. | 128/419 PG |
| 4,543,954 | 10/1985 | Cook et al. | 128/419 PG |
| 4,550,732 | 11/1985 | Batty, Jr. et al. | 128/419 PG |
| 4,562,840 | 1/1986 | Batina et al. | 128/419 PG |
| 4,596,251 | 6/1986 | Plicchi et al. | 128/419 PG |
| 4,719,920 | 1/1988 | Alt et al. | 128/419 PG |
| 4,722,342 | 2/1988 | Amundson | 128/419 PG |
| 4,763,655 | 8/1988 | Wirtzfeld et al. | 128/419 PG |
| 4,771,780 | 9/1988 | Sholder | 128/419 PG |
| 4,782,836 | 11/1988 | Alt | 128/419 PG |
| 4,807,629 | 2/1989 | Baudino et al. | 128/419 PG |
| 4,895,151 | 1/1990 | Grevis et al. | 128/419 PG |
| 4,926,863 | 5/1990 | Alt | 128/419 PG |

FOREIGN PATENT DOCUMENTS

| | | | |
|---|---|---|---|
| 0015779 | 9/1980 | European Pat. Off. | 128/419 PG |
| 0049812 | 4/1982 | European Pat. Off. | 128/419 PG |
| 0058603 | 8/1982 | European Pat. Off. | 128/419 PG |
| 0064002 | 11/1982 | European Pat. Off. | 128/419 PG |
| 0077844 | 5/1983 | European Pat. Off. | 128/419 PG |
| 0077845 | 5/1983 | European Pat. Off. | 128/419 PG |
| 0089014 | 9/1983 | European Pat. Off. | 128/419 PG |

(List continued on next page.)

OTHER PUBLICATIONS

Experience with a Two Sensor Controlled Rate-Adaptive Pace Maker System by H. Heuer et al., vol. 6, No. 2/86, Jun. 1986, pp. 64-67 (Eng. trans.).

(List continued on next page.)

*Primary Examiner*—Francis Jaworski
*Assistant Examiner*—George Manuel
*Attorney, Agent, or Firm*—Frishauf, Holtz, Goodman & Woodward

[57] ABSTRACT

A pacemaker has means for producing first and second signals one of which changes rapidly in response to changes in exercise level but may inaccurately represent the appropriate pacing rate. Such signal may be derived from a vibration sensor. The second signal accurately represents the required pacing rate but changes slowly in response to exercise level and may represent any of a number of different physiological variables, such as respiratory rate. The signals may be derived from the same or separate sensors. A control circuit provides a pacing rate appropriate to resting conditions if the first signal has a value less than a threshold regardless of the value of the second signal. The pacing rate is elevated to a predetermined level, such as 95 beats/min, if the first signal exceeds the threshold but the second signal has a value indicative of a pacing rate less than the predetermined level. The pacing rate is further elevated to substantially equal that indicated by the value of the second signal when the first signal exceeds the threshold and the second signal indicates a rate higher than the predetermined rate.

7 Claims, 6 Drawing Sheets

FOREIGN PATENT DOCUMENTS

| | | | |
|---|---|---|---|
| 0107483 | 5/1984 | European Pat. Off. | 128/419 PG |
| 0114679 | 8/1984 | European Pat. Off. | 128/419 PG |
| 0140472 | 5/1985 | European Pat. Off. | 128/419 PG |
| 0160801 | 11/1985 | European Pat. Off. | 128/419 PG |
| 0178528 | 4/1986 | European Pat. Off. | 128/419 PG |
| 0191404 | 8/1986 | European Pat. Off. | 128/419 PG |
| 0201990 | 11/1986 | European Pat. Off. | 128/419 PG |
| 87/01947 | 4/1987 | European Pat. Off. | 128/419 PG |
| 0216725 | 4/1987 | European Pat. Off. | 128/419 PG |
| 0249818 | 12/1987 | European Pat. Off. | 128/419 PG |
| 0249820 | 12/1987 | European Pat. Off. | 128/419 PG |
| 0249821 | 12/1987 | European Pat. Off. | 128/419 PG |
| 0249824 | 12/1987 | European Pat. Off. | 128/419 PG |
| 0257116 | 3/1988 | European Pat. Off. | 128/419 PG |
| 0259658 | 3/1988 | European Pat. Off. | 128/419 PG |
| 81/01659 | 6/1981 | PCT Int'l Appl. | 128/419 PG |

OTHER PUBLICATIONS

Sensor Pacing, Research Leads . . . by Kenneth M. Anderson, Medical Electronics, Oct. 1986, pp. 89 to 93.

Present State and Future Trends . . . by M. Schaldach, Medical Progress Through Technology, vol. 13, 1987, pp. 85–102.

"Activitrax", Technical Manual–Models 8400/8402/8403.

Sensolog 703 Pulse Generator–Physician's Manual.

Temperaturgesteuerte Schrittmacherstimulation Erste Klinische Ergebnisse by E. Alt, "Zeitschrift fur Kardiologie", vol. 74, Settlement 5, Oct. 1985, p. 27.

Cardiac Pacemaker Regulated by Respiratory Rate and . . . by T. Segura et al., "Pace", vol. 11, Jul. 1988, pp. 1077–1084.

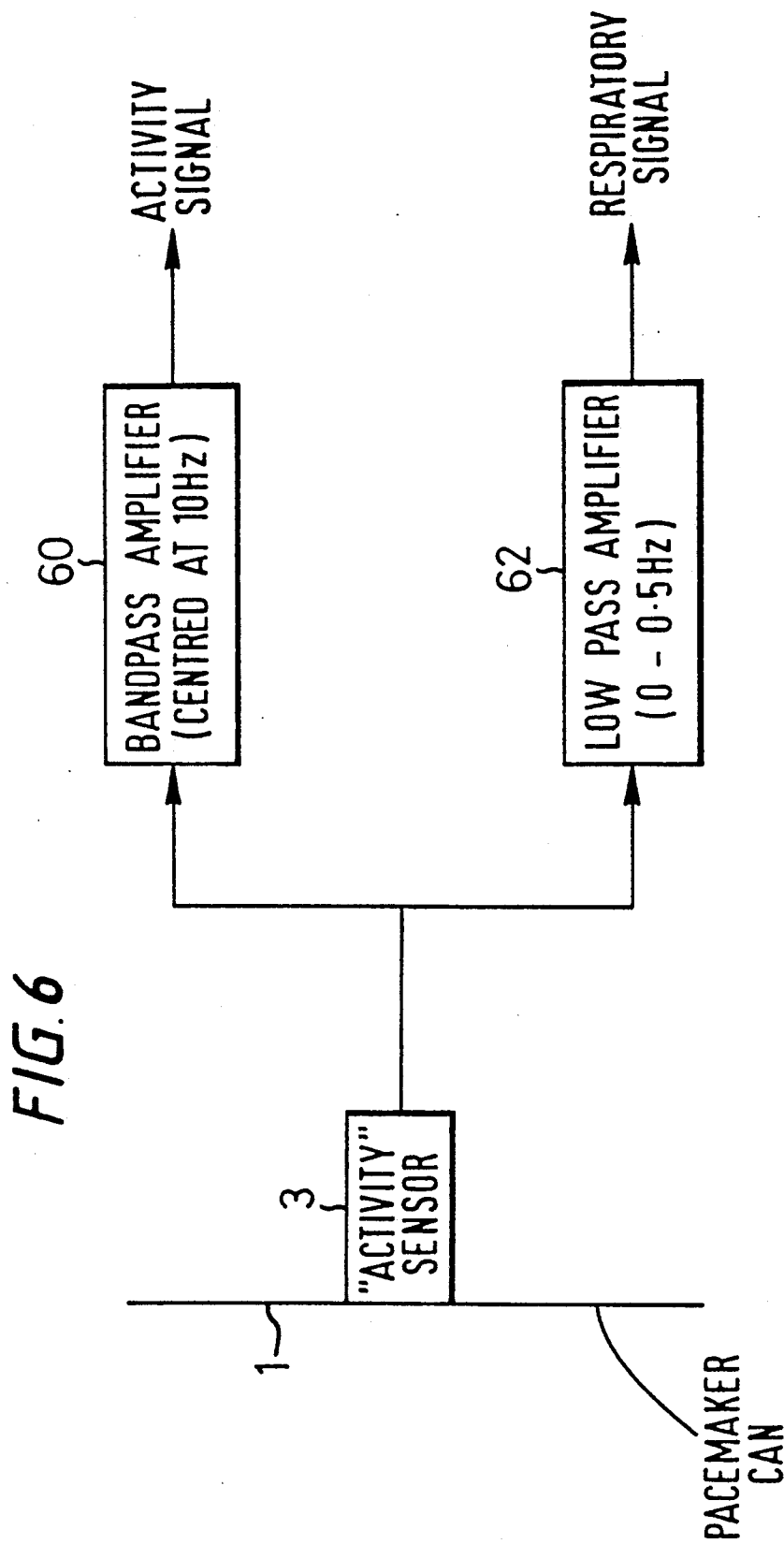

RATE-RESPONSIVE PACEMAKER

This is a continuation of application Ser. No. 07/311,638 filed July 16, 1989.

BACKGROUND OF THE INVENTION

The present invention relates to a cardiac pacemaker. In the normal healthy individual the output of blood by the heart is varied continuously to meet the metabolic demands of the body. The cardiac output changes with variations in the heart rate and the volume of blood pumped at each heart beat. The cardiac output is the product of these two variables. During strenuous exercise a four or five fold increase in cardiac output may be required. Approximately 75% of this increase is achieved by elevation of the heart rate.

Patients with cardiac disease resulting in very slow heart rates frequently require treatment in the form of an implanted artificial pacemaker. This consists of a small electrical pulse generator that is connected to the heart by an insulated electrode lead, usually positioned in the right ventricle.

Until recently the majority of such pacemakers were relatively simple devices that provided a constant frequency of stimulation. These suffer from the disadvantage that they are unable to increase the heart rate during exercise, thereby limiting the degree of exertion that the patient is able to undertake. This drawback has led to the development of two forms of pacemaker that can increase stimulation rate during exercise. The "ideal" system is a dual chamber pacemaker which has a second lead implanted in the right atrial chamber of the heart. This detects the rate of the heart's natural pacemaker and enables the artificial pacemaker to provide normal physiological changes in heart rate. However, such systems are not suitable for many patients and also have inherent technical and economic disadvantages.

An alternative approach that has been developed during recent years is the single chamber rate-responsive pacemaker. The fundamental principles of this device are as follows:

(A) A sensor is used to detect changes in a biological variable that are directly or indirectly proportional to the level of metabolic activity in the body. Evoked QT interval, respiratory rate, mixed venous temperature and body vibration are the main variables that are sensed by currently available rate-responsive pacemakers.

(B) The output from the sensor is processed by electronic circuitry to provide a signal that can be used to vary the stimulation rate provided by the pacemaker. This circuitry is designed to perform a series of mathematical and logical functions that are known collectively as the rate-response algorithm.

The two principal functions of the rate-responsive algorithm are:

(i) To determine the recognition level within the pacemaker for the value of the sensor signal which must be exceeded in order for an increase in pacing rate to be initiated (threshold level).

(ii) To determine the precise mathematical relationship between changes in the sensor signal S and the change in pacing rate P to be provided by the pacemaker, (the slope $dP/dS$).

Although every individual requires substantially the same heart rate as other individuals for a given level or type of physical activity, the changes which take place in the sensed biological variable as a result of a given level of physical activity differ from individual to individual. Accordingly, conventional rate response pacemakers are arranged so that the values of the threshold and slope may be adjusted to suit the individual patient. These values can be selected by telemetered instructions from an external programmer. The programmer is also used to select the minimum and maximum rates that the pacemaker will generate and to vary a number of other aspects of pacemaker function such as pulse amplitude and duration.

Conventional rate responsive pacemakers utilise a single biological sensor to modulate the pacing rate. Studies on the clinical performance of such pacemakers have revealed that no single sensor system is able to accurately reproduce the changes in heart rate that are seen in healthy individuals during the performance of normal daily activities. Thus pacing systems that detect movement of the body (e.g. by sensing physical vibrations) are able to provide correctly timed changes in hear rate but do not necessarily provide a response that is proportional to the degree of exercise that the user is undertaking. Pacing systems that indirectly detect changes in metabolic activity (e.g. by sensing the rate of respiration or the temperature of mixed venous blood) are able to generate changes in heart rate that are more physiologically appropriate in terms of their magnitude, but these responses may take place so slowly that they are too late to be of haemodynamic benefit to the user.

European Patent Application 249820 discloses an attempt at solving these problems. The pacemaker disclosed in that document includes several sensors each for sensing a respective different physiological variable and a selector circuit which successively selects different ones of the signals and/or combinations thereof in predetermined time steps after the start of an exercise cycle. In the example given, an acceleration sensor determines the start of an exercise period and controls the pacing rate during the initial portion of the exercise period which is predetermined and selected to be within the range 10 to 60 seconds. During the middle period of the exercise, which is predetermined and selected to be within the range 30 seconds to 20 minutes, a respiration sensor determines pacing rate. In the final period of the exercise which is also predetermined and selected to be within the range 30 seconds to 3 minutes, pacing rate continues to be determined by the respiration sensor. Although the European patent application also indicates that the selected signal and/or combination of signals may also be dependent upon other factors such as predetermined pacing rates, those output signals which fluctuate least, or the falling below a threshold of a single output signal or combination thereof, there is no specific description of what these dependencies might be in practice.

The present inventors consider that a pacemaker constructed as described in European Application 249820 would, in practice, suffer from disadvantages. For example, during the initial predetermined time period of the exercise, namely from 10 to 60 seconds, pacing rate varies with the magnitude of the signal from the accelerometer and thus, during this period, due to the deficiencies in such sensors, the actual pacing rate may differ substantially from the most appropriate pacing rate. For example, a person running downstairs may produce substantial vibration which would cause the accelerometer to produce a large output signal which in turn would cause the pacemaker to produce a higher pacing rate than actually required whereas a person running upstairs may produce less vibration, resulting in a lower pacing rate than actually required. Further, the predetermining of the lengths of the time periods in an exercise cycle during which different sensor signals are selected will mean that, in practice, where an individual undertakes a variety of different exercise cycles, the switching from one sensor signal to another may take place at inappropriate times.

Hertzschrittmacher, 6, 1986 pages 64 to 67 contains a report of some studies carried out into the possibility of providing a pacemaker with two sensors, one sensing bodily vibrations and the other central venous blood temperature. This study proposes that the advantages of the two systems can be obtained by utilizing the combination of such sensors and proposes that the pacing frequency increase should result from either a blood temperature increase or a change in the measured activity. In effect, therefore, this system would select a pacing rate equal to the higher of the rates indicated by the two sensors. In view of the inaccurate relationship between the magnitude of the signal output by a vibration sensor and required pacing rate, this system would not be satisfactory.

EP 259658 (Intermedics Inc) discloses a further attempt at solving the problem that vibration sensors, whilst responding rapidly to bodily vibrations, do not provide an accurate indication of the pacing rate required whereas sensors which sense such changes in metabolic activity as rate of respiration or mixed venous blood temperature respond slowly but, after response, may provide a signal which accurately indicates an appropriate pacing rate. EP 259658 suggests that filtering the output of a vibration sensor to suppress frequencies above approximately 4 Hz will provide a signal which not only responds rapidly to changes in bodily vibration but also has a "direct and substantially linear relationship" with the work being performed by the patient. The pacing rate is determined by an algorithm which utilises such a signal and a signal from a second sensor sensing, for example, blood temperature. This algorithm involves establishing a number of successively higher thresholds for the amplitude of the filtered signal from the vibration sensor and a number of fixed predetermined successively higher pacing rates associated with each threshold respectively. When the amplitude of the filtered signal from the vibration sensor exceeds a given threshold, the pacing rate is increased (at a predetermined rate of increase) to the respective value and counting of a predetermined time-out period is begun. If the signal from the second sensor (e.g. blood temperature sensor) increases within the time-out period to a level indicating that the required pacing rate is higher than the predetermined pacing rate associated with the relevant threshold, further increase in the pacing rate takes place in accordance with the level of the signal from the second sensor. If, however, the signal from the second sensor fails to increase to such a level within the time-out period, it is assumed that the increase in the filtered vibration sensor signal has been in error and a fault recovery program is executed to reduce the pacing rate back to a base level.

The algorithm disclosed in EP 259658 is also such that if the signal from the second sensor increases without the amplitude of the filtered signal from the first sensor having exceeded its first threshold some increase in pacing rate may take place under control of the signal from the second sensor, but this increase is limited to a small value. The description in EP 259658 appears to envisage that, under conditions where the amplitude of the filtered signal from the first sensor has exceeded a given one of the thresholds, the further increase in pacing rate which may take place under control of the second signal (provided it has increases sufficiently within the time out period) is limited to a small value so that the higher pacing rates can only be achieved if the filtered vibration sensor signal first exceeds successively higher thresholds.

Regardless of whether filtering out frequencies above 4 Hz in a signal derived from a vibration sensor would actually provide a signal substantially linearly related to the work being performed by a patient as suggested in EP 259658, the proposal in this patent suffers from a number of problems.

Firstly, the setting up of even a single threshold is a relatively complicated and skilled operation requiring the patient to undergo selected exercises whilst a skilled technician or physician monitors the operation of the pacemaker in order to enable him to program in an appropriate threshold. The setting of a number of successively high thresholds, therefore, would be extremely complex and time consuming and the present inventors believe that it may in fact be impossible to achieve a satisfactory set of such thresholds in the majority of patients. Further complexity arises in the need for setting time-out periods and the need for defining the small amounts of increase in pacing rate which may take place if the second signal increases without the amplitude of the filtered vibration sensor signal having first exceeded an appropriate threshold.

Secondly, the algorithm disclosed in EP 259658 is such that a number of common activities could not be adequately provided for. One example is any form of exercise that generates significant body vibrations but does not require high levels of energy expenditure, e.g. brushing one's teeth. Such a form of exercise will generate high amplitude vibrations in the frequency range of 1–4 Hz. These will be detected by the activity sensor and cause a rapid rise in pacing rate as a number of vibration threshold levels are exceeded. The complementary sensor will not indicate the need for a pacemaker rate response and will eventually ensure that the pacemaker rate returns to near base levels. However, this decline in rate will not occur until the termination of the time out period, and will thus not prevent a period of excessive pacing rate occurring which may last for two or three minutes, for example. Another example is any form of exercise that requires a high level of energy expenditure by the patient but does not generate high amplitude vibration signals, e.g. swimming. In this situation it is likely that only a lower vibration threshold level will be exceeded, resulting in a small increase in pacemaker rate. The rate will of course increase further during sustained exertion when the ongoing energy expenditure is detected by the complementary sensor, but it appears that the algorithm of EP 259658 will limit the magnitude of this secondary rise in pacemaker rate if the vibration signal remains small.

SUMMARY OF THE INVENTION

The invention, at least in its preferred embodiment, aims to solve the above problems. The way in which this solution is achieved by the invention will be understood by considering the following description.

In a preferred aspect, the present invention provides a rate responsive pacemaker that incorporates two distinct modalities of biological sensing. These two modalities may be detected by means of two separate sensor systems or they may be derived by electronic processing of the signal from a single sensor. In order to simplify the description of the present invention it will be assumed that two separate sensors are required. Signals from the two sensors will be analysed simultaneously by a dual-channel rate response algorithm. This algorithm is designed to retain the beneficial aspects of the responses provided by each different sensory modality while at the same time minimising their adverse aspects.

The two sensors will be termed Sensor 1 and Sensor 2. It must be emphasized that Sensor 1 can in practice be any sensor that provides an immediate response to a change in the level of physical exertion being performed by the user whereas Sensor 2 can be any sensor that accurately determines the magnitude of this change. However, for the purposes of the following description, it will be assumed that Sensor 1 detects body vibration and Sensor 2 measures the rate of respiration.

Sensor 1 serves to detect whether or not the user is undertaking physical exertion of sufficient magnitude to necessitate an increase in heart rate. During a sustained period of physical inactivity, the lack of a signal from Sensor 1 will keep the entire rate response algorithm in a "deactivated" state, thereby allowing the pacemaker to function "on demand" at a preset minimum rate. In this state, signals from Sensor 2 will be ignored and will thus be incapable of initiating "unwanted" increases in pacing rate (e.g. as may occur with hyperventilation in the absence of physical exertion).

With the onset of physical exertion, however, Sensor 1 will detect the increased amplitude and magnitude of body vibrations and when these exceed a preset threshold value, the rate response algorithm will be activated. A first channel (Channel 1) of the algorithm will initiate an increase in pacing rate. This response will be of an "all or none" character in that the pacing rate will rise progressively until a predetermined upper rate limit is reached. For the purposes of this document it will be assumed that the response will take the form of a linear increase in rate with a gradient of 1 beat/min/sec. The resting pacing rate may be 70 beats/min and the upper rate limit should preferably be at least 20 beats/min higher than the resting rate and preferably not more than 30 beats/min higher than the resting rate. It is particularly preferred that the upper rate limit be 25 beats/min higher than the resting rate, namely 95 beats/min when the resting rate is 70 beats/min. It should be understood, however, that these values are given by way of example. It should, however, be understood that a particularly preferred aspect of the invention involves the provision in channel 1 of a single threshold, which threshold is selected to represent an exercise level requiring an increase of at least 20 beats/min relative to the resting rate.

The pacing rate will remain elevated for as long as sensor 1 continues to detect supra-threshold body vibrations. As described above, the highest pacing rate that can occur solely as a result of activation of Sensor 1 is say 95 beats/min. A provision of the current invention is that the signals detected by Sensor 2, in effect, serve to modulate this upper rate limit.

The output from Sensor 2 will be fed to a second channel (Channel 2) of the rate response algorithm. This channel will incorporate circuitry that can assess the rate and/or depth of respiration and thereby determine a pacing rate that is physiologically appropriate for the level of exercise being undertaken by the users. If the signals from Sensor 2 are such that a rate of less than the upper rate limit of Channel 1, e.g. 95 beats/min, is indicated, the pacemaker will continue to function at the rate (e.g. 95 beats/min) as determined by Channel 1 of the rate response algorithm. If the signal from Sensor 2 indicates a rate that is higher than the Channel 1 maximum (e.g. 95 beats/min), however, then this rate will be adopted by Channel 1 as a revised upper rate limit. The pacemaker rate will rise progressively until this new upper limit is attained. A programmable "maximum upper rate" value will be employed to ensure that the pacing rate cannot rise to levels that would adversely influence cardiovascular function and thereby have deleterious consequences for the user.

A drop in the level of exercise will be detected by Sensor 2 and this will in turn lead to a lower rate being generated by Channel 2 of the algorithm. This will reduce the upper rate limit for Channel 1 and a corresponding drop in pacing rate will follow. If the level of exercise declines to such an extend that the vibration signals detected by Sensor 1 fall below the preset threshold, the entire algorithm will return to the "deactivated" state. In this state, the pacing rate will fall progressively until the minimum rate of 70 beats/min is reached. It is envisaged that a constant rate of decline of pacing rate will be provided under these circumstances, and a possible value for this rate of decline would be 0.5 beats/min/sec. It therefore follows that the higher the pacing rate is at the moment of cessation of exercise, the longer it will take for the pacing rate to decline to the resting level.

Applicants also acknowledge the disclosure of European Patent Application 191404 which discloses a pacemaker utilising an activity sensor (i.e. a vibration sensor) and a physiological sensor. In order to converse the battery, the physiological sensor and associated circuitry is normally turned completely off. However, if the activity sensor produces a signal higher than a given threshold, then the physiological sensor and associated circuitry is turned on and pacing rate controlled, at all times, in accordance with the magnitude of the signal from the physiological sensor. The sole object of the arrangement disclosed in European Application 191404 is to converse the battery and this document does not address the problems with which the present invention is concerned.

BRIEF DESCRIPTION OF THE DRAWINGS

The invention is described further, by way of example, with reference to the accompanying drawings, in which:

FIG. 6 is a block diagram showing a modification to the preferred embodiment.

DETAILED DESCRIPTION OF THE PREFERRED EMBODIMENTS

Figure 1:
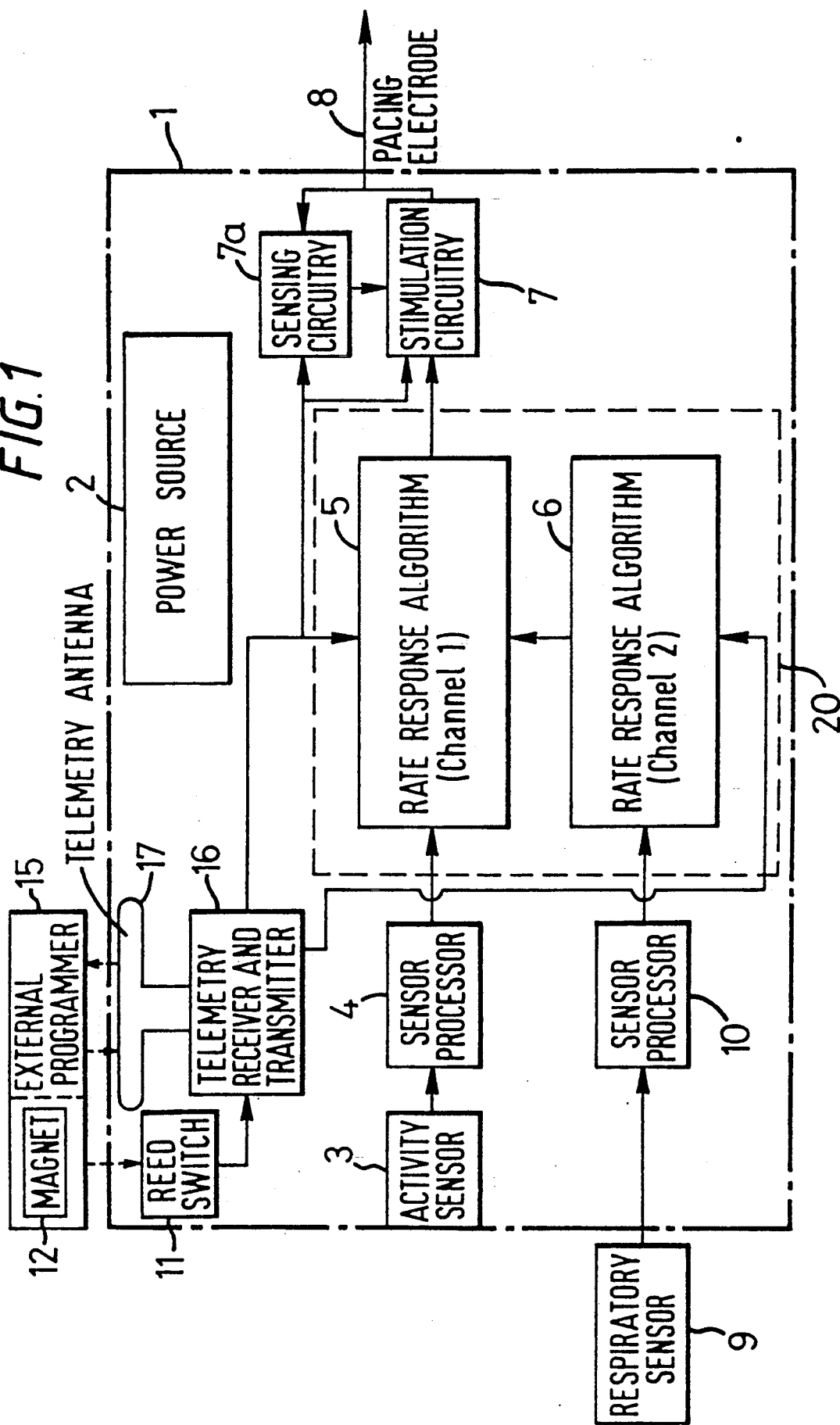
FIG. 1 is a functional block diagram illustrating a preferred embodiment of the present invention.

The illustrative implantable rate responsive pacemaker shown in FIG. 1 comprises a hermetically sealed can 1 containing a power source 2 (e.g. a battery), an activity sensor 3, an activity sensor processor 4, circuitry 5 and 6 defining two channels of a rate response algorithm, and stimulating circuitry 7. A lead 8 extends through the wall of the can to a pacing electrode (not shown) for applying an electrical stimulus to the heart of the user of the pacemaker. A respiratory sensor 9 is situated outside the can and is connected to a respiratory sensor processor 10 within the pacemaker.

The activity sensor 3 is sensitive to the level of physical vibration within the user's body. It generates an activity signal that is amplified and processed by processing circuitry 4 before being passed to circuitry 5 that constitutes channel 1 of the rate response algorithm. Under resting conditions, this channel of the algorithm defines a constant minimum pacing rate by means of a pacing control signal that is applied to the stimulation circuitry 7. The value of this minimum pacing rate, and other required values to be described below, can be selected by means of a telemetry signal from an external programming unit 15. Thus, the can 1 contains a telemetry receiver and transmitter device 16 having an antenna 17 so that information may be exchanged with the external programmer 15. A feed switch 11 is provided in the can 1 for activating the device 16 in response to the proximity of a magnet 12 provided in the external programmer 15.

When the user performs physical exercise, the amplitude and frequency of the activity signal will increase. When the amplitude and/or frequency of the signal exceeds a preset threshold value, channel 1 of the rate response algorithm will respond by increasing the rate of the pacing control signal. The activity signal threshold value may be selected by means of a telemetry signal from the external programming unit.

The resulting increase in the rate of the pacing control signal will be in the form of an "all or none" response. The rate will rise progressively from the preset minimum value until a preset upper rate limit is reached (for example, the rate will rise linearly by 1 beat/min/sec from 70 beats/min up to 95 beats/min). Having reached the upper rate limit, the pacing control signal of Channel 1 will remain at this level for as long as the activity signal remains above its threshold value.

If the level of physical exertion being undertaken by the user declines to such an extent that the activity signal falls below its threshold value, the entire rate response algorithm will return to a "deactivated" state and the rate of the pacing control signal will fall progressively to the preset minimum value (for example, it will decline linearly by 0.5 beats/min/sec until a rate of 70 beats/min is reached).

The respiratory sensor 9 detects changes in the electrical impedance of the user's chest wall. Chest wall impedance varies with respiratory movement, and the user's respiratory rate at any given moment is represented by the number of cyclical variations in impedance that are occurring per minute. The signal representing these impedance changes is amplified and processed by sensor processor 4 before being analysed in channel 2 of the rate response algorithm. If the amplitude of this impedance signal falls below a predetermined threshold level, it will be rejected by the rate response algorithm. Under these circumstances, the upper rate limit of channel 1 of the algorithm will remain unchanged.

However, if the amplitude of the impedance signal exceeds the threshold value, channel 2 of the algorithm will respond and increase its output rate. The mathematical relationship between the change in the frequency of the respiratory sensor signal (and thus a change in the rate of respiration) and the subsequent change in algorithm output rate is set by a predetermined slope value. Values for both the respiratory threshold and the respiratory slope can be selected using telemetry signals from the external programming unit. In clinical use, values will be selected by the physician so that channel 2 of the algorithm will produce an output rate that is physiologically appropriate for the user's rate of respiration (and hence appropriate for the level of physical exercise he is undertaking).

If the channel 2 output rate is less than the initial upper rate limit of channel 1 of the algorithm (for example, less than 95 beats/min), then the upper rate limit of channel 1 will remain unchanged. If the channel 2 output rate exceeds this value, however, then the upper rate limit of channel 1 will be raised accordingly. Thus, in effect, the upper rate limit of channel 1 of the rate response algorithm is modulated by the output of the channel 2 of the algorithm. There will be a ceiling rate that the upper rate limit cannot exceed, and this value will be selected by a telemetry signal from the external programmer.

The pacing control signal produced by channel 1 of the rate response algorithm is fed to conventional pacemaker stimulation circuitry 7. Sensing circuitry 7a is employed to monitor the user's intrinsic cardiac behaviour. If the user's heart beats spontaneously at a rate higher than that determined by the pacing control signal, the output of the pacemaker stimulation circuitry will be inhibited. The pacemaker will thus function "on demand" in that it will only stimulate the user's heart to beat if the inherent natural heart rate falls below the physiologically appropriate rate (as determined by the rate response algorithm).

Stimulation circuitry 7 is employed to deliver impulses of predetermined amplitude and duration to the user's heart via a conventional unipolar or bipolar transvenous pacing lead 8. The rate at which these impulses are delivered is determined by the pacing control signal and the timing of impulse delivery may be influenced by the pacemaker sensing circuitry.

The rate response algorithm circuitry 5, 6 may be switched into a permanently "deactivated" state by means of a telemetered instruction from the external programing unit 15. In this state the incoming signals from both biological sensors will be ignored and the pacemaker will continue to function "on demand" at the preset minimum pacing rate.

The telemetry reception/transmission circuitry 16 may be conventional and will be used to control the following aspects of pacemaker function:

(a) Mode, namely "Demand, Fixed Rate" or "Demand, Rate Responsive", (b) Minimum pacing rate—for both modes.

(c) Maximum pacing rate—for "Rate Response" mode only.

(d) Activity sensor threshold value.

(e) Respiratory sensor threshold value.

(f) Respiratory slope value.

(g) Pacemaker stimulation and sensing parameters—including stimulus amplitude and duration, refractory period, and sensitivity.

(h) Telemetry function—to enable the pacemaker to transmit the values of all programmable parameters out to the external programmer.

Figure 2:
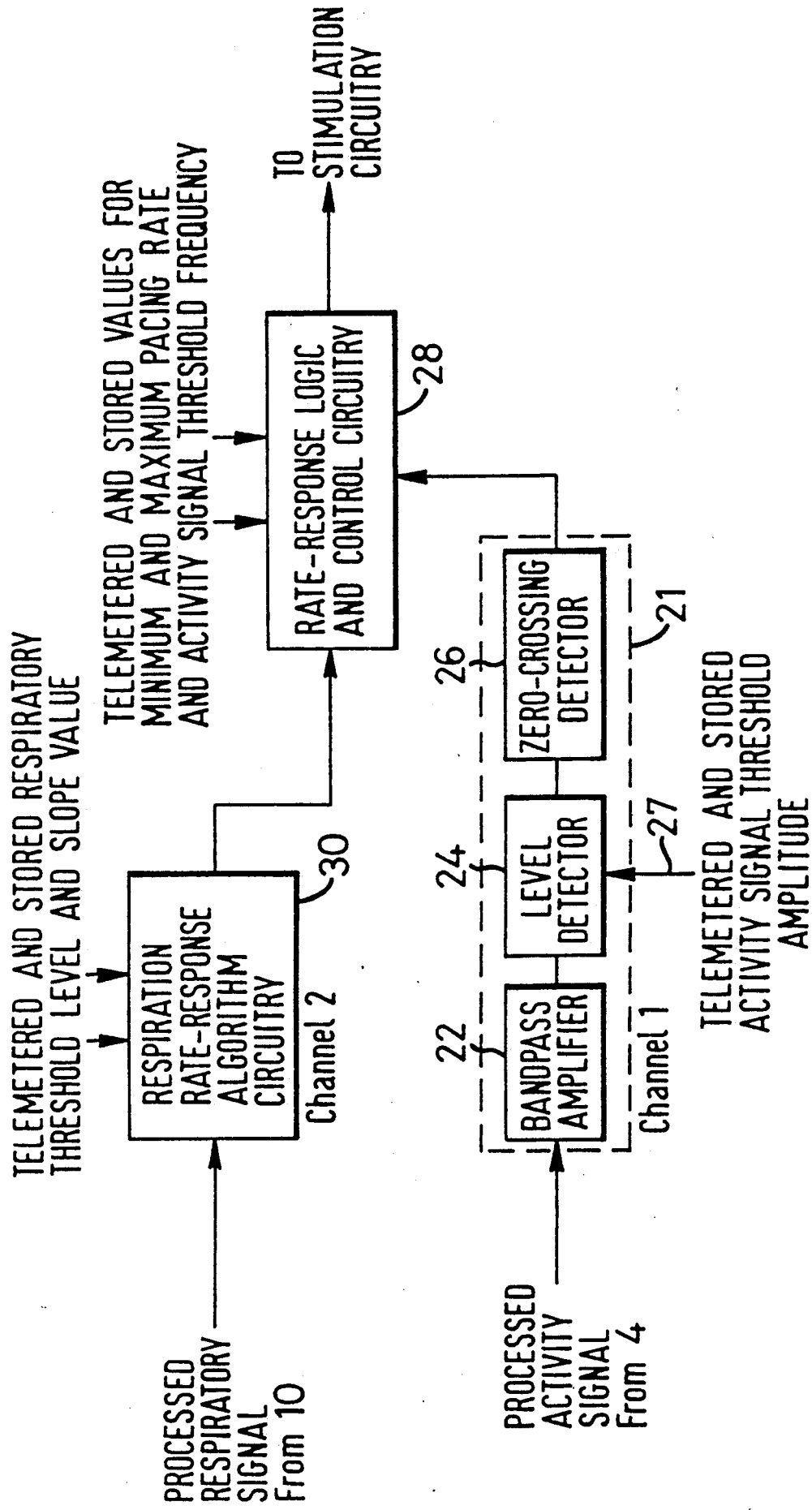
FIG. 2 is a block diagram showing part of the embodiment of FIG. 1 in more detail.

FIG. 2 illustrates in more detail the circuitry enclosed within broken line 2 of FIG. 1, in accordance with a preferred embodiment of the invention. As shown in FIG. 2, the signal from the activity sensor 3, after processing in circuitry 4, is applied to circuitry 21 which may be in accordance with U.S. Pat. No. 4,428,378 (Anderson et al), the contents of which are incorporated herein by reference, and thus may comprise a band pass amplifier 22, level detector 24 and zero crossing detector 26. If the amplitude of the signal supplied by the amplifier 22 to the level detector 24 exceeds a threshold defined by a signal supplied on line 27 to circuitry 21 from the telemetry receiver and transmitter circuitry 16, zero crossing detector 26 outputs a series of pulses at a frequency indicative of the level of activity sensed by the activity sensor 3. These output pulses are supplied to a rate-response logic and control circuit 28.

The signal from respiratory sensor 9 and processing circuitry 10 is applied to circuitry 30 defining the respiration rate response algorithm. This circuitry may be in accordance with U.S. Pat. No. 4,567,892, the contents of which are incorporated herein by reference, and has stored therein respiratory threshold and slope values received from the telemetry device 9. The output of circuitry 30 is also supplied to the rate-responsive logic and control circuit 28.

Circuit 28 has stored therein values for minimum and maximum pacing rate received from the telemetry device 16 and is operative to perform the above described functions. These functions may be provided by hardware or software or a combination of both but, in the present embodiment, it will be assumed that circuit 28 includes a microprocessor which is programmed to carry out the required functions in accordance with the flow chart shown in FIG. 3.

Figure 3:
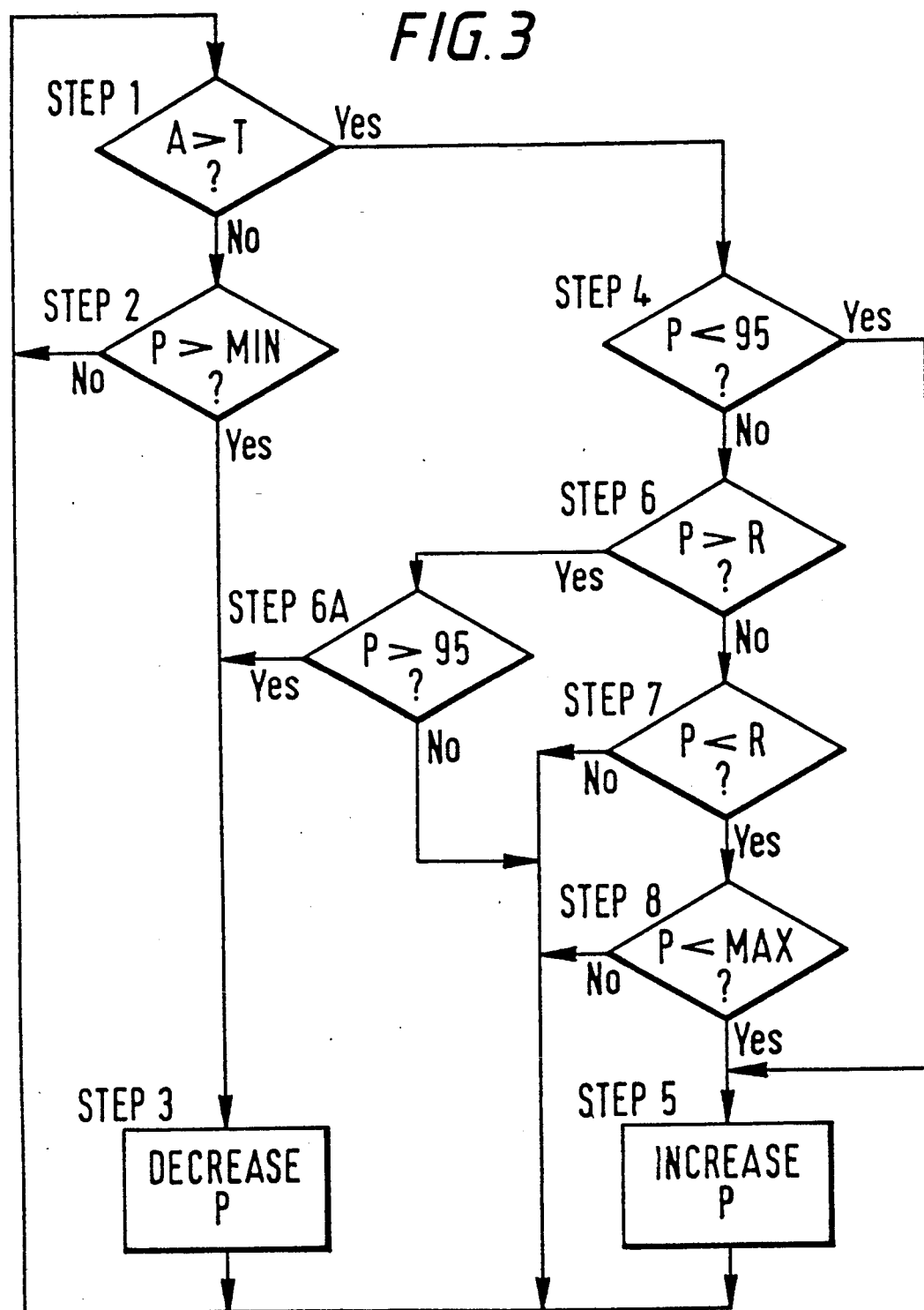
FIG. 3 is a flow chart showing the functions performed in the preferred embodiment of the invention.

In FIG. 3, the frequency of the signals from circuit 21 is represented by A, and T represents the threshold frequency thereof which defines the level of activity above which pacing rate will be increased. The actual current pacing rate is represented by P and the signal output by circuit 30, representing the pacing rate indicated by the respiratory sensor, is represented by R.

At step 1 in FIG. 3, the microprocessor determines whether the frequency of activity signal A is greater than the threshold T. In this embodiment, this determination is preferably made by counting the number of pulses received by circuitry 29 from zero—crossing detector 26 in a preselected period of time. In this way, circuitry 28 determines whether the frequency of the pulses output by sensor 4 having an amplitude above the level set by level detector 24 is greater than the selected threshold frequency T. If A is less than T, step 2 determines whether the pacing rate is greater than the minimum pacing rate stored in circuitry 28. If it is not, the program returns to step 1 without changing the pacing rate. If it is, the program moves to step 3 which initiates a decrease in the pacing rate, at a fixed rate such as 0.5 beats/min/sec. Following this initiation, the program returns to step 1 and the decrease in P continues, at the fixed rate, with the program moving through steps 1, 2 and 3 until such time as step 2 indicates that P is not greater than the minimum. At this time, the decrease is stopped and the program loops to step 1.

If, at any time, step 1 indicates that A is greater than T, the program branches to step 4 which determines whether the actual pacing rate is less than a predetermined level stored in circuitry 28 and indicted as being 95 beats/min. If step 4 indicates that P is less than 95 beats/min, the program moves to step 5 which initiates an increase in P at a fixed rate, such as 1 beat/min/sec. Following this initiation, the program loops back to step 1 and continues to move through steps 1, 4 and 5 until such time as step 4 indicates that P is not less than 95. At this time, the program branches to step 6 which determines whether the actual pacing rate is greater than the rate indicated by the respiratory sensor and circuitry 30. Normally, at the beginning of a period of exercise, there will be some delay before signal R increases beyond the level indicative of 95 beats/min so that, initially, it will be expected that step 6 will result in a "yes" and the program will move to step 6A which determines whether P is greater than 95 beats/min. As P will not have risen above 95 beats/min, this step will give a "no" and the program will continue to loop through steps 1, 4, 6 and 6A without further change of P. With sustained heavy exertion, R will increase until it exceeds 95 beats/min. When this occurs, step 6 will result in a "no", and the program will move to step 7. Step 7 is included to ensure that when P=R, the program will loop through steps 1, 4 6 and 7 without changing P. If R is greater than P, however, step 7 will result in a "yes". The program will move to step 8, where it is determined whether P is less than its permitted maximum value as stored in circuitry 28. If P is less than the maximum permitted value (as would be expected during the early stages of exercise), the program moves to step 5 whereby P is increased at the above mentioned fixed rate.

The program will continue to move through steps 1, 4, 6, 7, 8 and 5 in sequence until such time as steps 6 and 7 indicate that P is equal to R. When this condition occurs, the program will loop through steps 1, 4, 6 and 7 without further increase and without decrease in the actual pacing rate. If the level of physical activity is further increased so that R increases, step 7 will result in a "yes" and, so long as step 8 does not indicate that P has reached its maximum permitted value, a further increase in P, at the fixed rate above mentioned, will be initiated in step 5. If at any time, step 8 indicates that P has reached its maximum permitted value, further increases in R would not result in any further increase in P. If at any time, the level of physical activity decreases such that R becomes less than P, but does not decrease to an extent that A becomes less than T, the program will branch from step 6 through step 6A to step 3 so as to decrease the pacing rate P at the above mentioned fixed rate. This will continue until the rate P falls to 95 beats/min. At this time, step 6A will result in a "no" and step 3 will thereby be omitted from the loop, preventing a further decline in P.

The above sequence is continued until such time as the frequency A falls below the threshold T and/or the circuit 21 ceases to output pulses, due to the amplitude of the signal from amplifier 22 falling below the threshold stored in level detector circuitry 24. As a result, even though R may remain at a high level, the program moves from step 1 to step 2 at which it will be determined that P is greater than its minimum value and the program will then move to step 3, and loop through steps 1, 2 and 3, so as to reduce the pacing rate at the above mentioned fixed rate of reduction until such time as step 2 indicates that P is not greater than the minimum, whereafter the program will sequence through steps 1 and 2 until A again exceeds T.

It will be understood from the above description that pacing rate is only increased if both the amplitude of the signals from the activity sensor 3 exceeds a threshold defined by the level detector circuit 24 and the frequency of those signals exceeds the threshold frequency T. Thus, an advantage of the preferred embodiment of the invention is that undesired pacing rate increases do not arise either from isolated or low frequency signals of relatively large amplitude from the activity sensor 3 or from low amplitude relatively high frequency signals from the sensor 3.

It will be understood from consideration of the flow chart of FIG. 3 and the foregoing description that, after the pacing rate has been increased to the present level (95 beats/min in the example given) as a result of A exceeding T, all further increase in pacing rate is dependent solely upon the level of signal R derived from the second sensor. By this means, activities such as swimming may be adequately provided for since swimming may produce sufficient vibration for A to exceed T but would not produce sufficient vibration for A to exceed a significantly higher threshold. Further, activities such as brushing teeth producing high amplitude signals from the activity sensor would not result in an excessive increase in heart rate, which would be undesirable, since there would be no appreciable increase in the signal R derived from the second sensor. However, in the proposal in EP 259658, the high amplitude signals from the activity sensor would be expected to exceed several thresholds and therefore cause an excessive and undesired increase in heart rate. Further, with the present invention, upon the rapid onset of heavy exercise, the selected increase in pacing rate (25 beats/min giving a pacing rate of 95 beats/min in the example) may be such as to enable the patient to cope with such exercise for a period long enough to permit the signal from sensor 2 to catch up and then further increase the pacing rate as required. Since, in the embodiment under discussion, there is no time-out period within which the signal from sensor 2 must increase to any particular level, there is no risk of deactivating the algorithm with resultant reduction in heart rate as may arise in the arrangement disclosed in EP 259658 upon rapid onset of heavy exercise due to the inclusion of the timeout period.

Figure 4:
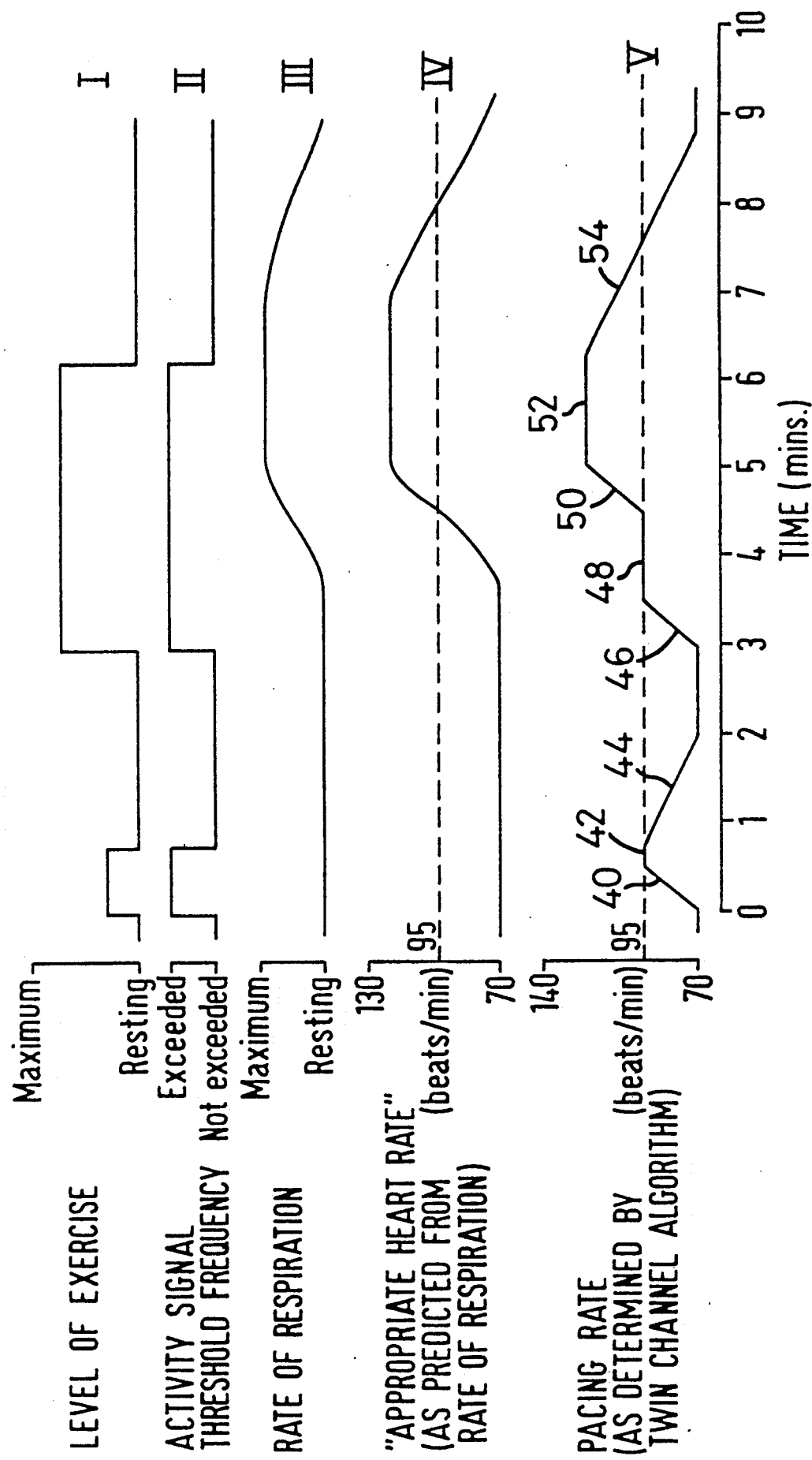
FIGS. 4 and 5 are graphs illustrating operation of the preferred embodiment of the invention.

FIG. 4 illustrates graphically the operation of the pacemaker according to the preferred embodiment as so far described and, by way of an example, illustrates a 10 minute period involving both periods of activity and of rest.

As shown in curve I of FIG. 4, the patient undergoes a relatively low level of exercise during the first minute, rests during the next two minutes, undergoes a much higher level of exercise during the following three minutes and thereafter returns to a condition of rest.

As shown by curve II, the level of exercise in each period is sufficient for the signal from the activity sensor and associated circuitry to exceed its threshold level.

There is a delay following the beginning of an exercise period before the patient's rate of respiration increases. Curve III shows that the first period of exercise, during which the exercise level is relatively low, is not long enough to cause the respiration rate to increase at all but the second period of exercise causes the respiration rate to increase, the increase beginning after a delay of about three-quarters of a minute from the beginning of the period of exercise.

Curve IV illustrates the pacing rate which the output of circuitry 30 indicates as appropriate. In view of the above mentioned delay, circuitry 30 does not indicate any increase in pacing rate during the first period of exercise and thus, if this alone were relied upon to control the pacemaker, no increase in heart rate at this time would result. This would be disadvantageous. Similarly, curve IV indicates that there is delay of about three-quarters of a minute after the beginning of the second period of exercise before circuitry 30 begins to indicate that the heart rate should be increased. Again, if the heart rate were not to be increased during this delay period, that would be disadvantageous.

Curve V shows that, despite the absence of a signal from circuitry 30 indicating that the heart rate should be increased during the first period of exercise, the pacing rate is nevertheless increased at a fixed rate as indicated at reference number 40. This increase arises from the program sequencing through steps 1, 4 and 5 illustrated in FIG. 3. As indicated by reference number 42 in curve 5, the pacing rate increases to a maximum level of 95 beats/min during the first period of exercise, this being achieved by the program sequencing through steps 1, 4, 6 and 6A.

Reference number 44 in curve V indicates that after the activity signal has fallen below the threshold, the pacing rate is reduced at the above mentioned fixed rate. This is achieved by the program sequencing through steps 1, 2 and 3 until the minimum rate of 70 beats/min is reached.

Reference number 46 in curve V shows that immediately the second period of activity begins, the pacing rate increases at the above mentioned fixed rate to 95 beats/min, as shown by reference number 48 and remains at that rate until there has been sufficient time for signal R to increase to a level indicating a rate greater than 95 beats/min, this taking about 1½ minutes in the example shown from the beginning of the second period of exercise.

Reference number 50 in curve V indicates that, after this point, the pacing rate P is increased, again at the same fixed rate as previously described, in response to the continuing increase in signal R. During the period corresponding to reference number 50, the program of FIG. 3 sequences through steps 1, 4, 6, 7, 8 and 5.

At some point, the signal R reaches the maximum value appropriate to the level of exercise being undertaken and, as indicated by reference number 52 in curve V, the pacing rate P is maintained constant at this maximum value. This is achieved by the program shown in FIG. 3 sequencing through steps 1, 4, 6 and 7.

As shown by reference number 54 in curve V, immediately the period of exercise terminates, the pacing rate begins to decrease at the above mentioned fixed rate since the activity signal drops below the threshold and the program sequences through steps 1, 2 and 3. This decrease takes place despite the fact that there is a delay before the respiration rate, and therefore signal R, decreases. Thus, the preferred embodiment of the invention provides a substantial advantage that the pacing rate begins to decrease immediately the exercise terminates rather than remaining at a high rate until such time as the respiration rate has decreased.

Figure 5:
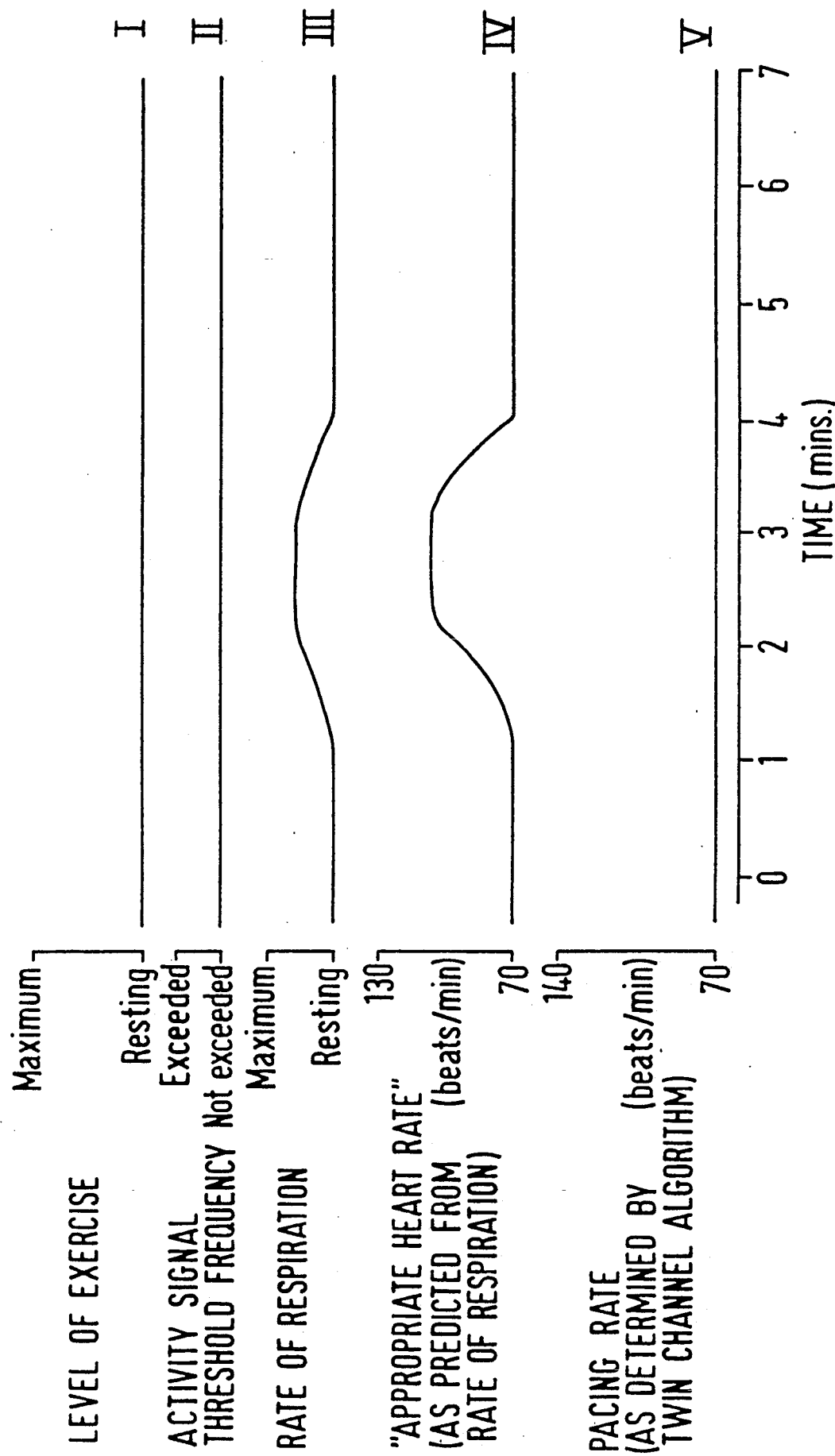

FIG. 5 is included to illustrate, with curves I to V which have the same meaning as curves I to V of FIG. 4, that from time to time, although the patient may not undergo any physical activity of significance so that there is no increase in the activity signal, respiration rate may nevertheless increase to a level such that the signal from circuitry 30 indicates that the pacing rate should be increased. However, in these circumstances, pacing rate increase is inappropriate and, as shown in FIG. 5, it does not in fact take place in the preferred embodiment of the invention since the program will remain sequencing through steps 1 and 2 until such time as the activity signal exceeds its threshold and regardless of the level of signal R.

Thus, in the invention the pacing rate is always substantially at the required level, any changes required begin to take place without any undesirable delay and the rate of change may be preselected and therefore selected to be optimum for increasing and optimum for decreasing rate. This combination of advantages is not achievable in the prior art.

In the modification shown in FIG. 6, the respiratory sensor 9 is omitted and instead a single activity or vibration sensor 3 is employed. The output from this sensor is applied to a band pass amplifier 60 centred at 10 Hz to provide an activity signal which is then supplied to sensor processor 10 and is also applied to a low pass amplifier 62 having a pass band of zero to 0.5 to provide a signal representing respiration rate which is applied to processing circuit 10. The sensor 3 may be as described in U.S. Pat. No. 4,428,378 and the circuitry shown in FIG. 6 enables that single sensor to provide both the activity signal and the respiratory signal, any unwanted cardiac signal being rejected. The modified embodiment illustrated in FIG. 6 is otherwise the same as the embodiment described with reference to FIGS. 1 to 5.

As will be appreciated, various modifications may be made within the scope of the invention. The various figures for increase or decrease of rate and maximum and minimum rate are merely given by way of illustration. For example, although the minimum rate has been given as 70 beats/min, it would be possible within the scope of the invention to provide for an extra reduction in rate to say 60 beats/min, where the patient is sleeping, this condition, for example, being indicated by the absence of any activity signal for a predetermined period of time. Thus, the reference to a minimum rate above should be understood as meaning the normal minimum rate, such as 70 beats/min. It is also within the scope of the invention for other values between the limit of say 30 to 100 beats/min to be chosen and telemetered into the pacemaker using the external programmer 15, the antenna 17 and receiving circuitry 16.

Further, although in the embodiment described with reference of the accompanying drawings, it has been assumed that detection of the frequency of signal A has been carried out by counting the number of pulses generated by zero crossing detector 26 in a predetermined period, other methods are possible. For example, the pulses output by the band pass amplifier could be integrated over a predetermined period and compared to an appropriate threshold.

In the above description, it has been indicated that the band pass amplifier 22 may pass signals within a band centered at 10 Hz. Typically, the bandwidth of this amplifier might be, say, 6 Hz whereby signals in the range 7 Hz to 13 Hz would be passed although alternative arrangements are possible, for example and band width of 4 Hz whereby signals in the range 8 to 12 Hz would be passed. It is not essential that the centre frequency of the band pass amplifier should be 10 Hz although this is a particularly preferred value. It might, for example, be lower or higher. The processing performed on the signal from activity sensor 4 should be such that the processed signal may be compared with a threshold which corresponds to a level of activity for which the appropriate pacing rate is preferably at least 20 beats per minute higher than the resting rate, for example 20 to 30 beats per minute higher than the resting rate and particularly preferably about 25 beats per minute higher than the resting rate. Thus a particularly preferred combination of features in accordance with the invention involves the detection of signals from the vibration sensor 4 having an amplitude above a predetermined level and a frequency of at least 7 or 8 Hz, and preferably 10 Hz, the circuitry causing an increase in heart rate of between 20 and 30 beats per minute, preferably 25 beats per minute above resting rate in response to the detection of such signals, further increases beyond this rate being under the sole control of the level of the signal from the second sensor.

The pacemaker according to the invention may be arranged for operation in any of a variety of different modes. For example, it may be used in the so-called AAI mode in which both pacing and sensing take place in the atrium and pacing pulses are inhibited if spontaneous activity is sensed, in the so-called VVI mode in which both pacing and sensing take place in the ventricle and pacing pulses are inhibited when spontaneous activity is sensed or the so-called DDD mode in which pacing and sensing take place in both the atrium and the ventricle with inhibition of the pacing pulses or triggering taking place in accordance with sensed activity, in a well-known manner.

Further, although in the preferred embodiment as described, the change in pacing rate takes place linearly with time, it is possible within the scope of the invention for the changes in pacing rate to take place non-linearly and it is possible for the changes to be made continuously or step-wise.

We claim:
1. A pacemaker comprising
means to control pacing rate by (a) rapidly responding to a change in a patient's exercise level as indicated by the value of a first signal representative of a first biological variable, and (b) following such rapid response, accurately setting the pacing rate relative to the patient's exercise level as indicated by the value of a second signal representative of a second biological variable;
a single sensor including means for measuring activity by the patient to produce an activity signal; and
signal processing means for generating said first and second signals from said activity signal.

2. An arrangement according to claim 1, wherein said first biological variable is bodily vibration and said second biological variable is a physiological variable.

3. An arrangement according to claim 2, wherein said sensor is a vibration sensor.

4. An arrangement according to claim 3, wherein said processing means comprises filtering means.

5. An arrangement according to claim 4, wherein said filtering means is operable to provide said first signal by passing a frequency band in the region of 10 Hz and to provide said second signal by passing frequencies less than about 0.5 Hz.

6. An arrangement according to claim 3, wherein said physiological variable is respiratory rate.

7. A cardiac pacer comprising:
(a) single means for sensing a plurality of signal variables indicative of a patient's biological parameters;

(b) said sensing means including output means for identifying and separating said signal variables;
(c) means coupled to said output means for selectively combining said separated signal variables in order to define a pacing rate of the cardiac pacer; and
(d) means coupled to said combining means for generating signals at said pacing rate.

* * * * *